United States Patent
Sankaridurg et al.

(10) Patent No.: US 11,567,347 B2
(45) Date of Patent: Jan. 31, 2023

(54) SYSTEMS, METHODS AND DEVICES FOR CONTROLLING THE PROGRESSION OF MYOPIA

(71) Applicant: Brien Holden Vision Institute Limited, Sydney (AU)

(72) Inventors: Padmaja Sankaridurg, Maroubra (AU); Thomas John Naduvilath, Glenfield (AU); Klaus Ehrmann, Queenscliff (AU); Fabian Conrad, Maroubra (AU)

(73) Assignee: Brien Holden Vision Institute Limited, Sydney (AU)

( * ) Notice: Subject to any disclaimer, the term of this patent is extended or adjusted under 35 U.S.C. 154(b) by 354 days.

(21) Appl. No.: 16/608,562

(22) PCT Filed: Apr. 27, 2018

(86) PCT No.: PCT/AU2018/050382
§ 371 (c)(1),
(2) Date: Oct. 25, 2019

(87) PCT Pub. No.: WO2018/195600
PCT Pub. Date: Nov. 1, 2018

(65) Prior Publication Data
US 2020/0183185 A1    Jun. 11, 2020

Related U.S. Application Data

(60) Provisional application No. 62/491,616, filed on Apr. 28, 2017.

(51) Int. Cl.
*G02C 7/02*    (2006.01)
*G02C 7/04*    (2006.01)
(Continued)

(52) U.S. Cl.
CPC ............. *G02C 7/041* (2013.01); *A61F 2/145* (2013.01); *G02C 7/027* (2013.01); *G02C 7/04* (2013.01);
(Continued)

(58) Field of Classification Search
CPC ...... G02C 7/041; G02C 7/06; G02C 2202/24; G02C 7/024; G02C 7/027; G02C 7/04;
(Continued)

(56) References Cited

U.S. PATENT DOCUMENTS

2004/0254420 A1    12/2004    Ward
2010/0296058 A1    11/2010    Ho et al.
(Continued)

FOREIGN PATENT DOCUMENTS

CN    103118627    5/2013
CN    203930244    11/2014
(Continued)

OTHER PUBLICATIONS

International Search Report dated Jul. 26, 2018 for PCT/AU2018/050382.
(Continued)

*Primary Examiner* — Jordan M Schwartz
(74) *Attorney, Agent, or Firm* — Jones Day

(57) ABSTRACT

An ophthalmic lens system for reducing the risk of progression of a myopic eye by selectively maintaining, inducing or creating asymmetry of the peripheral retinal profile for the eye. A method for reducing the risk of progression of myopia comprising determining the magnitude of asymmetry of the on-axis/off-axis refractive error profile or eye length profile of the eye and providing an ophthalmic lens system that corrects for and provides acceptable on-axis vision and simultaneously controls the position of the off-axis refrac-
(Continued)

tive error profile or eye length profile such that resultant profile of the eye is asymmetric.

14 Claims, 13 Drawing Sheets

(51) Int. Cl.
  *G02C 7/06* (2006.01)
  *A61F 2/14* (2006.01)
  *G16H 50/30* (2018.01)
(52) U.S. Cl.
  CPC ........... *G02C 7/06* (2013.01); *G02C 2202/24* (2013.01); *G16H 50/30* (2018.01)
(58) Field of Classification Search
  CPC ........ G02C 7/045; G02C 7/047; G02C 7/066; A61F 2/145
  See application file for complete search history.

(56) References Cited

U.S. PATENT DOCUMENTS

| | | | | |
|---|---|---|---|---|
| 2012/0116505 | A1* | 5/2012 | Shahinpoor | A61F 2/147 623/4.1 |
| 2012/0257161 | A1* | 10/2012 | Varnas | G02C 7/06 351/159.42 |
| 2013/0100398 | A1* | 4/2013 | Ryndin | G02C 7/024 425/500 |
| 2013/0182216 | A1* | 7/2013 | Ho | G02C 7/04 351/159.41 |
| 2015/0146164 | A1* | 5/2015 | Contet | G02C 7/028 351/159.42 |
| 2015/0320547 | A1* | 11/2015 | Rosen | A61F 2/1648 623/6.23 |
| 2015/0331255 | A1* | 11/2015 | Sankaridurg | G02C 7/06 351/159.75 |
| 2016/0320634 | A1 | 11/2016 | Ho et al. | |

FOREIGN PATENT DOCUMENTS

| | | |
|---|---|---|
| EP | 2415425 | 2/2012 |
| WO | WO 2006/004440 | 1/2006 |
| WO | WO 2012/034265 | 3/2012 |
| WO | WO 2015/106375 | 7/2015 |
| WO | WO 2017/222421 | 12/2017 |

OTHER PUBLICATIONS

Lundstrom, et al. Peripheral opital errors and their change with accommodation differ between emmetropic and optic eyes, Journal of Vision, Jun. 29, 2009, vol. 9, Jun., No. 17, pp. 1-11; Viewed on the internet Jul. 16, 2018, retrieved from the Internet URL:https//jov.arvojournals.org/article.aspx?articleid=2204011 Published online Jun. 1, 2009.

\* cited by examiner

| Patient | Eye | Ref. Error (D) | Eye Length (mm) | | | | | | | |
|---|---|---|---|---|---|---|---|---|---|---|
| | | | Nasal Retinal quadrant | | | Central | Temporal Retinal quadrant | | | |
| | | | 30° | 20° | 10° | | 10° | 20° | 30° | |
| 1 | RE | -2.75 | 23.79 | 24.24 | 24.50 | 24.63 | 24.73 | 24.67 | 24.37 | |
| 1 | LE | -3.50 | 23.77 | 24.34 | 24.65 | 24.81 | 24.90 | 24.54 | 24.14 | |

FIG. 6

Darker sections indicate relatively more positive power

SYSTEMS, METHODS AND DEVICES FOR CONTROLLING THE PROGRESSION OF MYOPIA

CROSS REFERENCE TO RELATED APPLICATION

This application is the National Phase application of International Application No. PCT/AU2018/050382, filed Apr. 27, 2018, which designates the United States and was published in English, which claims priority to U.S. Provisional Application No. 62/491,616, filed Apr. 18, 2017. Each of these applications, in their entirety, are incorporated herein by reference.

TECHNICAL FIELD

This relates to systems, methods, and devices for controlling the progression of myopia and more particularly to systems, methods, and devices for predicting the risk of progression of myopia and prescribing an ophthalmic device to control the progression of myopia.

BACKGROUND

Myopia (short-sightedness) is a disorder of the eye in which distant objects cannot be clearly focused, but near objects can be. Images of distant objects are brought to focus in front of the retina because the axial length of the eye is greater than the focusing power of the eye. Myopia may be corrected by the use of a negatively powered lens, which shifts the focus of the distant images to be on or nearer the fovea. For some individuals, myopia can be a serious and progressive condition that leads to increasing visual impairment despite the use of corrective lenses.

While there is general agreement that the process of normal eye development involves a feedback mechanism which regulates the length of the eye to maintain good focus for both distance and near objects, there is no consensus regarding the nature of the mechanism or how the mechanism decides on the magnitude of progression for each individual eye.

Accordingly, there is a need for systems, methods, and devices for determining the risk of myopia progression of each individual eye and/or to more effectively control the progression of myopia or a myopic shift in refractive error.

SUMMARY

Some embodiments described herein may provide systems, methods, and devices for predicting the risk of progression of myopia and/or prescribing an ophthalmic device to control the progression of myopia or a myopic shift in refractive error.

Some embodiments described herein may provide systems, methods and devices to identify the presence or absence of an asymmetric retinal profile to determine the risk of a myopic shift in refractive error.

In some embodiments, the systems, methods, and devices may benefit from utilizing the finding that refraction in central and peripheral areas of the retina of human eyes, or at least the eyes of a substantial or significant number of people, is such that the natural curvature of field of the peripheral retina is asymmetric around the visual axis (i.e., the axis being from the fixation point to the fovea) of the eye and eyes with more asymmetric retinal/ocular profile experience slower myopia progression than eyes with more symmetric retinal/ocular profiles. More specifically, in some embodiments, eyes of individuals with less myopia or smaller eye length in the nasal periphery of the eye relative to the temporal periphery or relative to the fovea may experience slower progression of myopia. More specifically, in some embodiments, eyes with asymmetry resulting in the nasal periphery (i.e., nasal retina) being less myopic or having smaller eye length compared to the refractive error and/or eye length at the fovea and/or temporal periphery may experience slower progression of myopia.

As a result, in some embodiments the control of on-axis and off-axis focal points of the eye may be such that an asymmetric refractive error and/or eye length profile is created to slow the progression of myopia or a myopic shift in refractive error. In other embodiments, the control of on-axis and off-axis focal points of the eye may be such that the asymmetric refractive error and/or eye length profile of the individual is maintained, or enhanced.

In some embodiments, treatment may include measuring the ocular characteristics of the eye at the fovea (in other words on-axis or at the central retina) and outside the fovea (in other words off-axis or at the peripheral retina) to determine the presence of asymmetry or symmetry of the refractive error and/or eye length profile of the eye. In some embodiments, ocular characteristics of the eye on-axis and/or off-axis may be measured through devices or instruments that may measure the refractive state of the eye at on-axis and/or off-axis positions or may be through devices or instruments that measure the eye length/shape of the eye at on-axis and/or off-axis positions.

In some embodiments, the eye of the individual may then be treated by modifying the refractive properties of the ocular system to provide substantially clear or acceptable vision on-axis and to control the position of the image at the peripheral retina to substantially create, maintain, or enhance the asymmetry of the refractive characteristics of the individual's eye. For an eye with asymmetry around the visual axis, a system with different refractive powers or different curvatures may be needed to maintain or enhance the asymmetry observed in different parts of the peripheral retina. In some embodiments, the refractive powers or curvatures may be selected such that it results in a shorter focal length or relatively more positive power for points on the nasal retina than for points on the fovea and/or the temporal retina. In other embodiments, the refractive powers or curvatures may be selected such that it results in a shorter focal length or relatively more positive power for one or more points on the nasal retina than for points on the fovea and/or the temporal retina. For an eye that is symmetrical around the visual axis, a device with different refractive powers or curvatures may be desirable to induce asymmetry at different parts of the peripheral retina relative to the fovea. In certain embodiments, asymmetry may be induced by selecting a refractive power or curvature that results in a focal length that is relatively more shorter or positive in power for points on the nasal retina than for points on the fovea and/or the temporal retina. In other embodiments, the refractive powers or curvature may be selected such that the eye receives relatively more positive refractive power or shorter focal length for one or more points on the nasal retina than for points on the fovea and/or points on the temporal retina. In certain other embodiments, the refractive powers or curvature may be selected that the eye receives varying amounts of relatively more positive power for one or more points on the nasal retina than the power at the fovea and/or the points at the temporal retina.

In some embodiments, the eye of the individual may then be treated by altering/modifying the ocular properties of the ocular system to control the position of the image at the peripheral retina to substantially create, maintain or enhance the asymmetry of the shape or eye length of the individual's eye.

One way of modifying the refractive properties is through the use of an ophthalmic device (e.g., a lens). Embodiments of a device for an eye may include contact lenses, spectacle lenses, corneal implants or other lenses that have different power profiles for images received by different parts of the peripheral retina. The class of contact lenses may include lenses that operate by having a refractive power and orthokeratology lenses that achieve a change in the refractive properties of the eye by reshaping the cornea. In other embodiments, the ocular characteristics of the eye may be modified through the use of devices and surgical procedures such as retinal implants and posterior eye surgery that selectively induce asymmetry across the central and peripheral retina.

In some embodiments, a lens may be provided for affecting the progression of myopia in an eye. The lens may comprise a nasal optic zone and a temporal optic zone for refracting light to be received by the peripheral retina. The nasal optic zone and temporal optic zone may have different refractive powers or curvatures selected such that the nasal retina is more myopically defocused than the temporal retina at positions equally removed from the fovea (e.g., at 20 or 30 degrees). The lens may further include a central optic zone with a refractive power or curvature to correct, substantially correct, and/or sufficiently correct for the refractive power of the eye on-axis and to provide clear or acceptable distance vision at all or substantially all distances.

In some embodiments, a method of prescribing an optical device and/or procedure for affecting images received by the peripheral retina may include observing whether the recipient of the optical device has a substantially symmetrical or asymmetrical curvature of field. The prescribed optical device and/or procedure may then be selected to either adjust the peripheral image symmetrically or asymmetrically dependent on the observation such that the refractive or ocular characteristics of the patient's eye are created, maintained or enhanced.

Other features and advantages of the subject matter described herein will be apparent from the description and drawings, and from the claims.

BRIEF DESCRIPTION OF THE DRAWINGS

Aspects of the embodiments described herein may be best understood from the following detailed description when read with the accompanying figures.

FIG. 6 illustrates measurements of eye length at 30° degrees, 20° degrees and centrally in both nasal and temporal meridians using the technique/device described in connection with FIG. 6.

DETAILED DESCRIPTION

Figure 1:
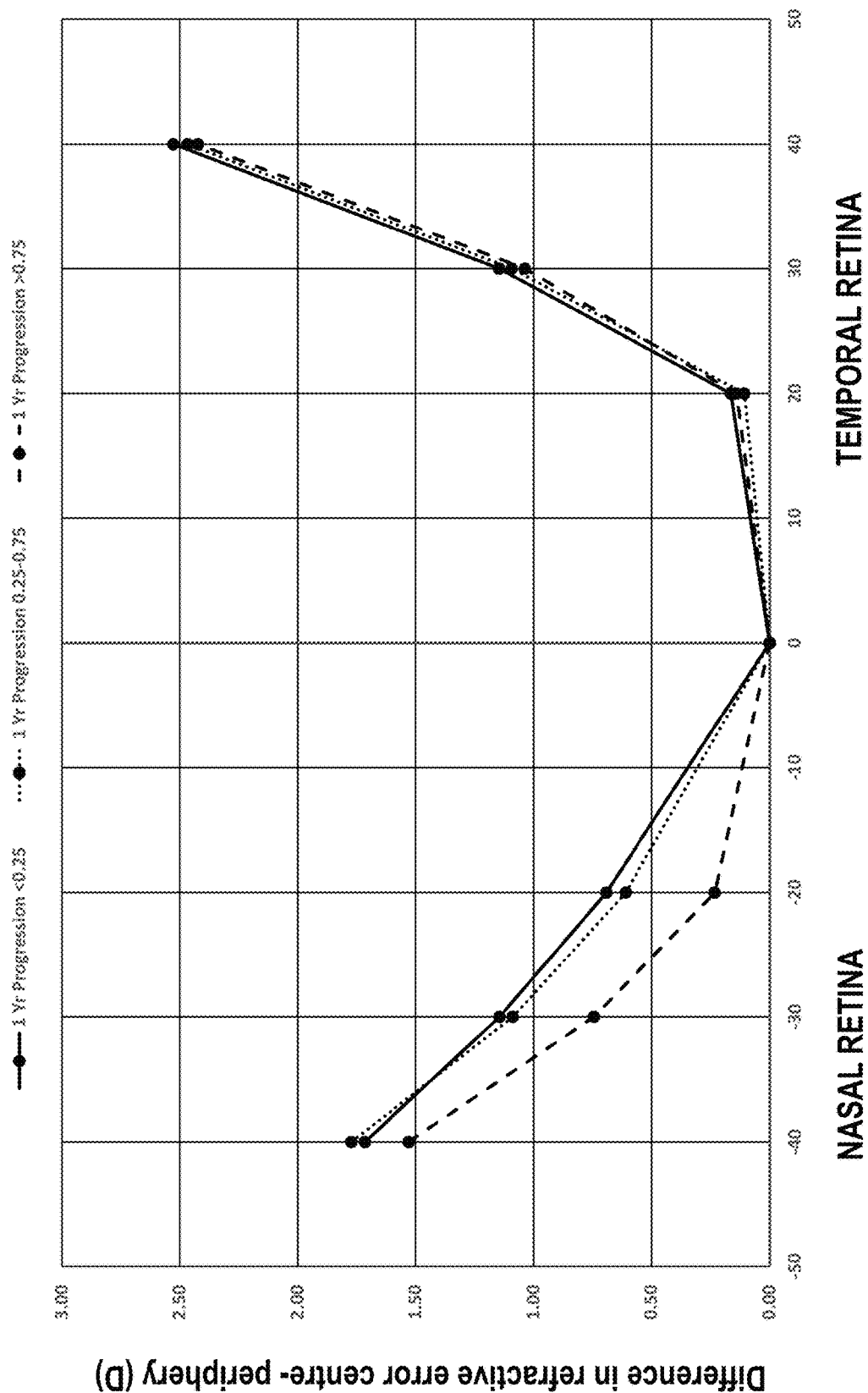
FIG. 1 is a plot illustrating asymmetry in the nasal versus temporal peripheral retina for a sample group of eyes of individuals with myopia.

The following disclosure provides many different embodiments, or examples, for implementing different features of the provided subject matter. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. As used herein, temporal visual field corresponds to the nasal retina and nasal visual field corresponds to the temporal retina. Myopia progression can lead to increasing visual impairment despite the use of corrective lenses.

In a study conducted of more than 1000 eyes over a 12 month period of time, a significant relationship has been identified between the refractive error at the nasal retina of an individual to that of the refractive error at the fovea and the temporal retina, and the amount of myopia progression. In particular, the relationship identified indicated that individuals with lesser myopia progression (e.g., lesser than 0.75 diopters in 12 months) had relatively less myopia at the nasal retina compared to central on axis refractive error or the refractive error measured at the temporal retina than those that progressed more (e.g., more than 0.75 diopters in 12 months). In other words, individuals who had little to no progression had a more asymmetric relative peripheral refractive error profile than those who progressed more significantly.

FIG. 1 shows a plot of the refractive state for more than 1000 eyes of individuals with myopia at the peripheral retina in the horizontal meridian, with measurements for both the nasal and temporal quadrants taken. The horizontal axis indicates the peripheral angles at which measurements were taken. Measurements at the nasal retina represent the temporal visual field and measurements at the temporal retina represent the nasal visual field. The vertical axis is the amount of refractive error (defocus), in diopters (D), relative to the amount of refractive error (defocus) along the visual axis (e.g., fovea) of the eye. Accordingly, positive values indicate relative less myopia relative to center or on-axis refractive error and negative values indicate more myopia relative to center or on-axis refractive error. Measurements of defocus were taken on axis and at 20, 30 and 40 degrees from the optical axis, both temporally and nasally.

The eyes were divided into three groups—a group that experienced a one year progression of less than 0.25 diopters (solid line), a group that experienced a one year progression of between 0.25 diopters and 0.75 diopters (dotted line), and a group that experienced a one year progression of more than 0.75 diopters (dashed line).

As illustrated, there was relatively little difference between the three groups at the temporal retina at any of the peripheral angles. However, in the group that experienced more than 0.75 diopters of progression (dashed line), the peripheral refractive error profile (nasal to temporal) was substantially more symmetrical at 20 degrees than the other two groups. This suggests a correlation between the symmetry of the refractive error profile of the eye and the progression of myopia. In particular, this data suggests that eyes with a relatively more asymmetric refractive error profile at about 20 degrees of nasal-temporal retina experience less progression of myopia over time.

Figure 2:
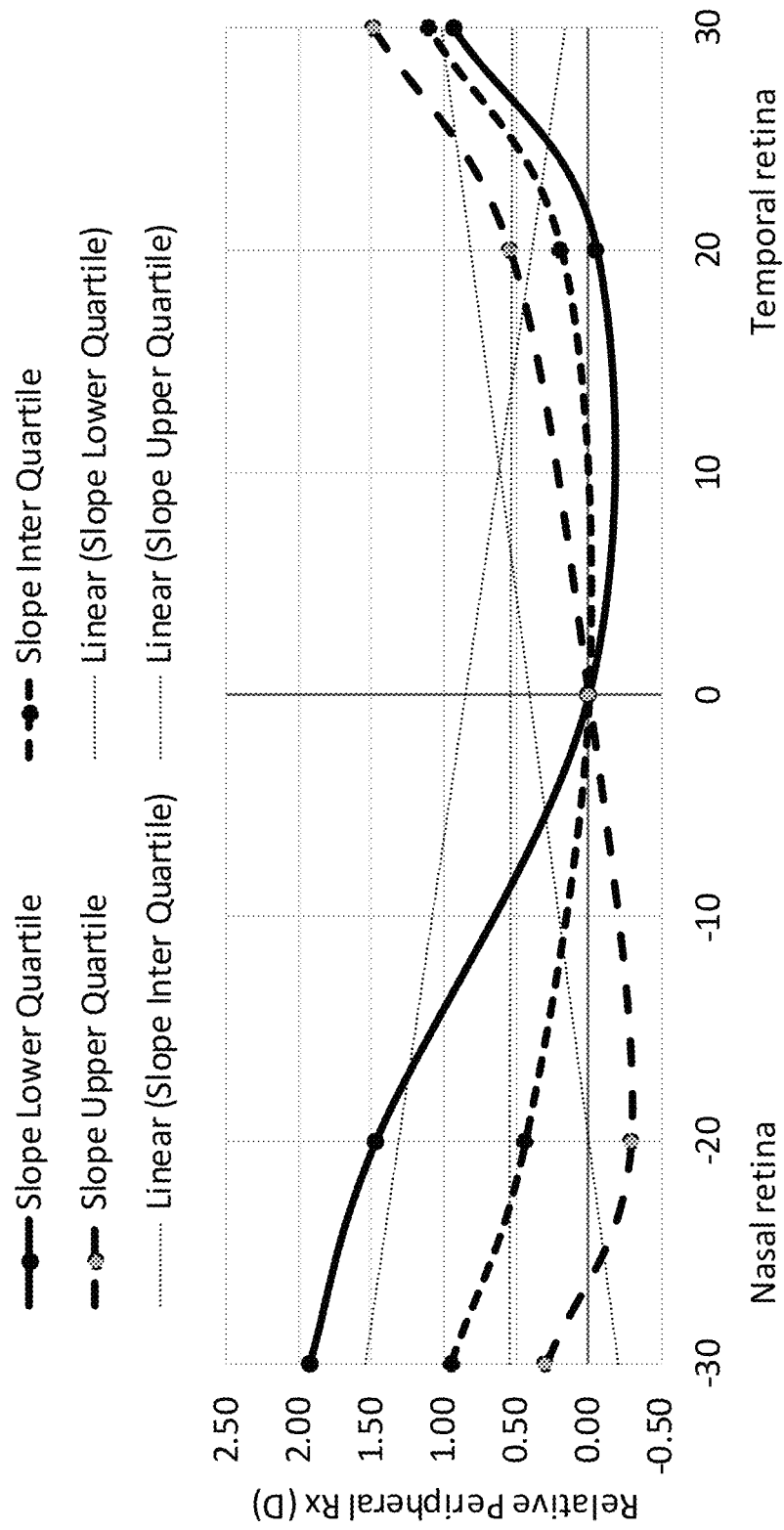
FIG. 2 is a plot of the slope of the relative peripheral refractive error profile (from 30 degrees nasal retina to 30 degrees temporal retina) as determined for 3134 eyes and with the eyes categorized into the lower, middle and upper quartiles.
Figure 3:
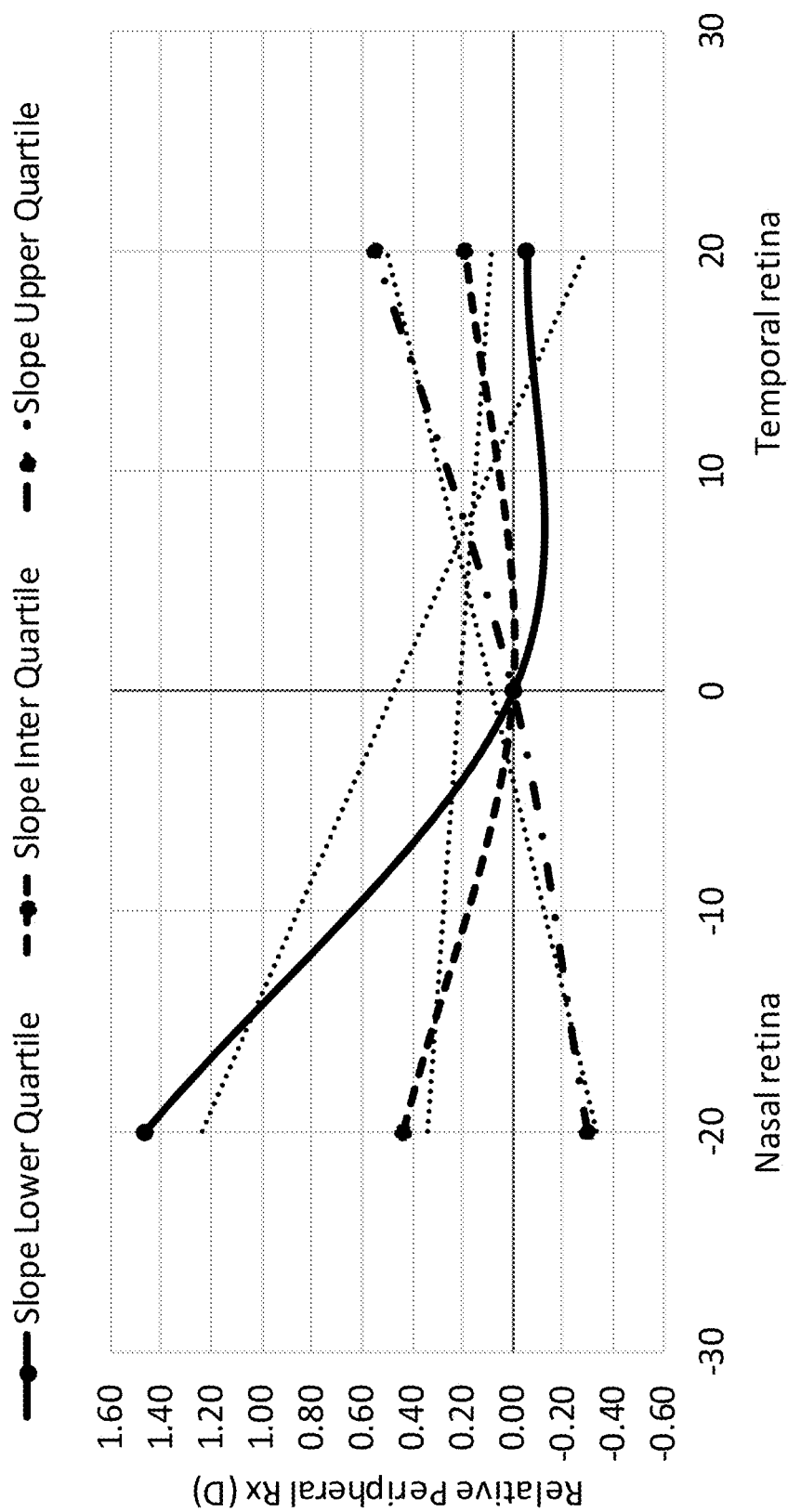
FIG. 3 is a plot of the slope of the relative peripheral refractive error profile (from 20 degrees nasal retina to 20 degrees temporal retina) as determined for 3134 eyes and with the eyes categorized into the lower, middle and upper quartiles.

The refractive error profile of 3134 eyes at the baseline visit was determined by measuring refractive error at 30° degrees, 20° degrees and centrally in both nasal and temporal quadrants in the horizontal meridians. Thereafter the refractive error profile relative to center (relative peripheral refractive error profile) between 30 degrees temporal and nasal retina and between 20 degrees temporal and nasal retina was determined and the slope of the relative refractive error profile was also determined. FIG. 2 shows the slope (from 30° nasal retina to 30° temporal retina) and FIG. 3 shows the slope (from 20° nasal retina to 20° temporal retina) and with the eyes categorized into the lower, middle and upper quartiles. For each eye, relative to central refractive error, peripheral refraction at 30 degrees nasal (−30), 20 degrees nasal (−20), 20 degrees temporal (+20) and 30 degrees temporal (+30) retina was used to determine asymmetry, defined as the slope (D/degree) of a linear fit using a least squares method. The slope measures the rate of change in diopters per unit change in horizontal eccentricity. A zero slope indicates perfectly symmetrical peripheral refractive error profile. A negative slope indicates that the peripheral refraction at 20 degrees temporal field (nasal retina) was more hyperopic (less myopic) than at 20 degrees nasal field (temporal retina). A positive slope indicates that the peripheral refraction at 20 degrees temporal field (nasal retina) was more myopic/less hyperopic than at 20 degrees nasal field (temporal retina). Based on each eye's slope coefficient of the peripheral refractive profile, eyes were categorized into lower, middle and upper quartiles. Majority of eyes in the lower quartile would likely have a negative slope and majority of eyes in the upper quartile would likely have a positive slope.

Slope between temporal and nasal visual fields is given as $$\frac{\sum_{i=-30}^{30} ((x_i - x_m)(y_i - y_m))}{\sum_{i=-30}^{30} (x_i - x_m)^2}$$

Where $x_i$ is the visual field angles (−30, −20, −10, 0, 10, 20, 30) and $x_m$ is 0

Figure 4:
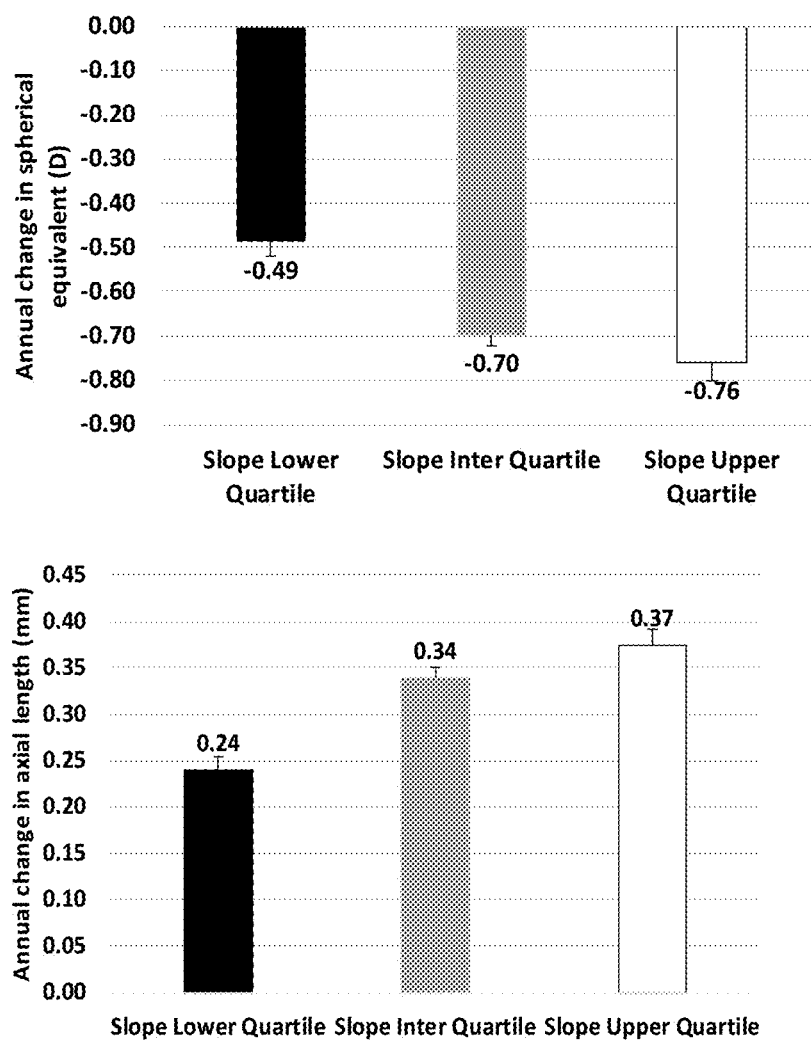
FIG. 4 is a chart illustrating that at a 1 year follow-up as compared to the baseline slope profile, eyes with slope in the lower quartile progressed less compared to those in the middle and upper quartile whereas those in the middle quartile progressed less than those in the upper quartile.

$y_i$ is the relative peripheral refraction at each peripheral retinal angle $y_m$ is the average relative peripheral refraction The progression of myopia at 1 year was then compared to baseline slope profile and as seen from FIG. 4, eyes with slope in the lower quartile progressed less compared to those in the middle and upper quartile whereas those in the middle quartile progressed less than those in the upper quartile.

Figure 5:
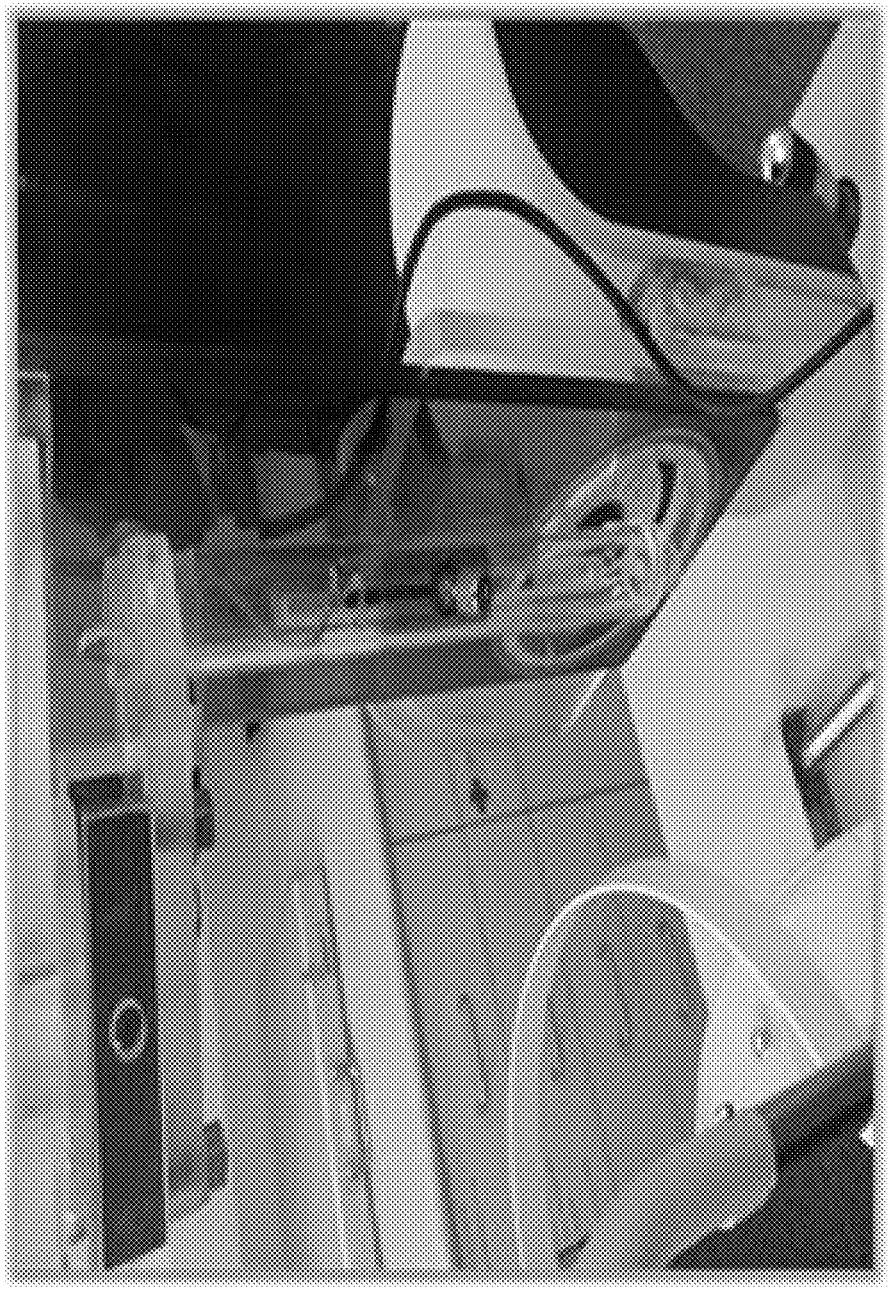
FIG. 5 illustrates an attachment coupled to a device that may be used to measure eye length at central (on-axis) and peripheral (off-axis) locations.

FIG. 5 shows an attachment coupled to a device that may be used to measure eye length (LENS STAR) to determine presence or absence of asymmetry. In operation, an individual is seated in front of the instrument with their head and chin appropriately positioned. For central eye length measurement, the individual is asked to look and fixate at an internal fixation light of the instrument. For measurements of peripheral eye length along various meridians (i.e. horizontal), the attachment provides a fixation target corresponding to the corresponding peripheral retinal location and the individual is asked to rotate their eyes to locate and fixate on the appropriate target. The eye length may be measured at various locations (e.g., corresponding to 10, 20 and/or 30 degrees in the nasal and/or temporal horizontal meridians).

FIG. 6 illustrates measurements of eye length at central and peripheral points for an adult myopic eye with moderate myopia (patient 1). In some embodiments, the measurements may be obtained using the instrument described with reference to FIG. 6. As illustrated, the axial length at nasal retina is shorter in comparison to that observed at the temporal retina for both eyes for this particular patient.

Accordingly, in some embodiments, predicting the risk of progression of myopia may include determining the presence or absence of asymmetry between the temporal retina and nasal retina (e.g. at about 20 to 30 degrees from the fovea) and evaluating the magnitude of asymmetry to determine if an individual is a) at the risk of progression of myopia and b) if the risk of progression of myopia is relatively low or high. In certain embodiments, predicting the risk of progression of myopia may include evaluating the magnitude of asymmetry between the temporal retina and the fovea alone or in combination with other determinations, or evaluating the magnitude of asymmetry between the nasal retina and the fovea alone or in combination with other determinations. In certain other embodiments, predicting the risk of progression of myopia may include evaluating the magnitude of asymmetry between the nasal retina and the fovea by measuring the nasal retina at one field angle or more than one field angle. In some embodiments, measuring the asymmetry between the fovea and nasal retina may be accomplished by determining the difference between the refractive error at the nasal retina, and/or determining the difference in the eye length at the fovea and the eye length at the nasal retina, and/or determining the difference in eye shape from the fovea to the nasal retina. In some embodiments, the relevant comparison may be between the central fovea and the nasal retina. In other embodiments, the relevant comparison may be between the nasal retina and the temporal retina. In other embodiments, the relevant comparison may be between the nasal retina and the rest of the retina (i.e. fovea and temporal retina).

In some embodiments, the measurements may be taken using e.g., an open field Shin Nippon autorefractor utilizing head-turn or eye turn for off-axis measurements. In other embodiments, the measurements may be taken with a device to measure eye length on-axis and at various angles off axis for example using an IOLMaster or LensStar. In certain other embodiments, the eye shape may be measured using for example, ultrasound or magnetic resonance imaging.

Accordingly, in some embodiments, the systems, methods, and devices described herein may involve the design and/or prescription of ophthalmic systems or devices taking into account the understanding that eyes which experience less myopia at the nasal retina than the temporal retina may experience slower progression of myopia.

In other words, by accounting for the asymmetry of the eye, the relative curvature of field of the eye can be controlled in a manner such that the peripheral image is (or remains) asymmetrical.

In some embodiments, the ophthalmic system and/or device may be configured to utilize the existing asymmetry of the eye and in some embodiments, the ophthalmic system and/or device may be configured to enhance (or introduce) asymmetry into the eye to control (e.g., slow) the progression of myopia. In certain other embodiments, the ophthalmic system and/or device may be configured to induce myopic defocus at the nasal retina relative to on-axis or central refractive error to induce asymmetry at the nasal retina. In certain other embodiments, the ophthalmic system and/or device may be configured to induce greater myopic defocus at the nasal retina relative to retinal defocus at the temporal retina to induce asymmetry at the nasal retina. In other embodiments, the ophthalmic system and/or device may be configured to induce myopic defocus at the nasal retina relative to the on-axis or central refractive error and may have the same magnitude of myopia defocus as the temporal retina. In some embodiments, the optical zone of the ophthalmic lens system and/or device that corresponds to image formation at the nasal retina may be configured to have a shorter focal length relative to the optical zone that corresponds to image formation at the central and/or temporal retina. Particularly, the temporal optical zone of the ophthalmic lens system and/or device is configured to have a shorter focal length relative to the focal length of the central optical zone and/or nasal optical zone to induce asymmetry at the nasal retina.

FIGS. 7-10 illustrate examples of contact lenses with asymmetric profiles in accordance with some embodiments described herein. In particular, these figures show examples of the general structure of four different contact lenses 100, 200, 300, 400, for controlling the relative position of peripheral images of an eye to maintain or enhance the asymmetry of the nasal to temporal retina of an individual. In general, the lenses 100, 200, 300, 400 are for a left eye and have different focal lengths in a region on the nasal side than that on the temporal side. A design for the right eye may be a mirror image in structure, but the power profile resulting in a focal length in each optic zone will be selected dependent on the characteristics of the right eye. Each lens has an optic zone 101, 201, 301, 401, which may be between approximately 6 to 8 mms (e.g., approximately 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, or 8 mm) (e.g., between approximately 6-6.5 mm, 6.25-6.75 mm, 6.5-6.7 mm, 6.75-7.25 mm, 7-7.5 mm, 7.25- 7.75 mm, or 7.50-8 mm) in diameter, depending on the particular implementation. Outside the optic zone 101, 201, 301, 401 is a carrier portion 102, 202, 302, 402, which provides stability for the lens when applied to the eye. The carrier portion may for example extend for another 4 to 8 mm, so that the total lens diameter up to the lens edge 106, 206, 306, 406 may be about 14 mm. Other embodiments may have differing dimensions, and particular dimension lenses may in some cases be selected according to the eye to which the lens is to be applied, for example to reflect differences in size of the pupil 50. In FIGS. 7-10 the outer periphery of the carrier zone is represented in dashed lines.

The lenses are oriented on the eye with the utilization of a suitable lens stabilization technique. The desirability to stabilize the orientation of the lens arises since the power of the contact lens varies across the surface and is affected to ensure application of power to selected regions of the central and the peripheral regions of the retina. The lenses may be stabilized on eye with a lens stabilizing mechanism selected from a prism ballast, double slab-off and truncation etc.

Figure 7:
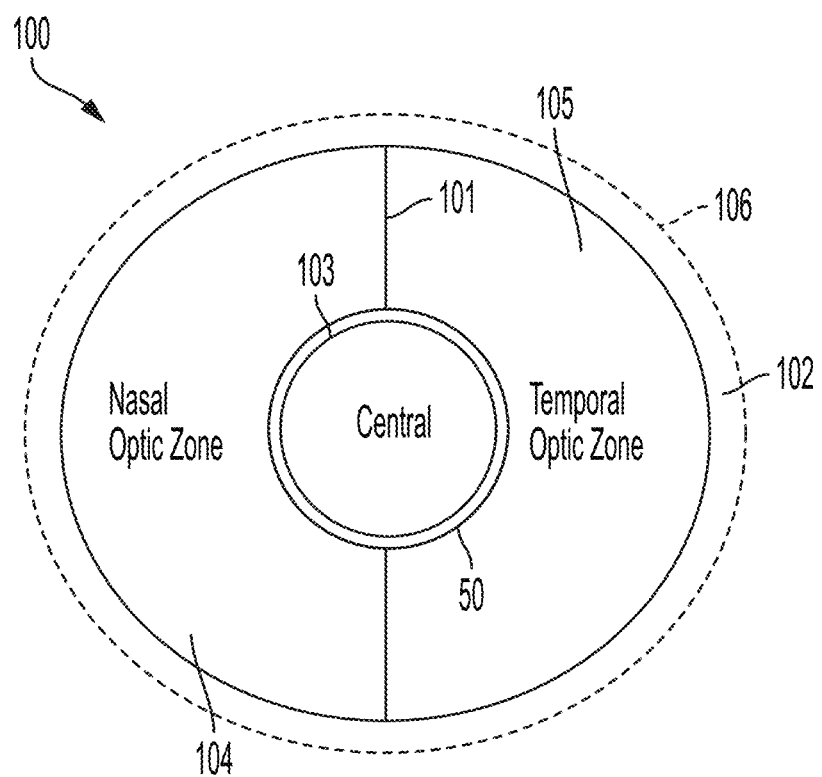
FIG. 7 illustrates an example of a contact lens with asymmetric profiles in accordance with some embodiments described herein.

In the example shown in FIG. 7 the lens 100 has a disc-shaped central optic zone 103. The central optic zone 103 has a diameter selected from the range of from about 0.5 mm up to about 3 mm (e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm) (e.g., about 0.5-1 mm, 0.75-1.25 mm, 1-1.5 mm, 1.25-1.75 mm, 1.5-2 mm, 1.75-2.25 mm, 2-2.5 mm, 2.25-2.75 mm, or 2.5-3 mm). The central optic zone 103 is located and provided with a refractive power that determines the focal length that corrects for the central refractive error of the eye (measured at the fovea). With this selection of power, the central optic zone 103 allows for clear vision at all or substantially all distances (assuming that the eye can accommodate to provide in focus near vision). The power profile of the lens varies between the nasal optic zone 104 and temporal optic zone 105 on either side of the central optic zone 103. The nasal optic zone 104 is designed to address the defocus at the temporal retina and the temporal optic zone is designed to address the defocus at the nasal retina. The power in these zones is selected to correct for the defocus measured in the temporal and nasal quadrants of the peripheral retina respectively while maintaining or enhancing an asymmetry between the nasal retina and the temporal retina.

In some embodiments, these zones may carry a single refractive power that corrects for the average defocus measured at the peripheral retina over a range of field angles. Thus for example, in these embodiments the nasal optic zone 104 will correct for defocus experienced by the peripheral retina on the temporal side. Similarly, the temporal optic zone 105 will correct for the defocus experienced by the peripheral retina on the nasal side. The amount of correction will depend on the relative means measured for the nasal retina and temporal retina and selected to maintain an existing asymmetry or adjusted to induce or enhance the asymmetry to a desired level to control the progression of myopia.

In some embodiments, the nasal and temporal optic zones 104, 105 may carry a plurality of refractive powers or curvatures, selected with regard to the defocus measured at two or more locations of the peripheral retina. For example, the focal length and therefore the refractive power or curvature of the nasal optic zone may be set taking account of the relative defocus experienced by the temporal peripheral retina at 20, 30 and 40 degrees and include a smooth transition between the powers required at these angles. If measurements are taken for an eye at more angles or at only two angles, then the refractive power or curvature may be set in the nasal and temporal optic zones 104, 105 having regard to those measurements. The variation may reflect the measured curvature of field of the eye to which the lens is to be applied. For example, a lens may be selected with a power profile or curvature profile across the nasal optic zone 104 that has the objective of a substantially constant distance between the focal point and the retina. Similarly variations in power profile or curvature may occur across the temporal optic zone. Again, the amount of correction will depend on the relative errors measured for the nasal retina and temporal retina and should be selected to maintain an existing asymmetry or adjust the asymmetry to a desired level to control the progression of myopia. In some embodiments, the power profile or curvature of the central optical zone, nasal optical zone and the temporal optical zone of the ophthalmic lens may be selected such that the magnitude of asymmetry between the nasal retina and the central and/or temporal retina is about 0.75 D or more. In other embodiments, the power profile or curvature of the central optical zone, nasal optical zone and the temporal optical zone of the ophthalmic lens may be selected having given consideration to the population averages such that the magnitude of asymmetry between the nasal and temporal optical zones is about 1.50 D or more, about 1.25 D or more, about 1.00 D or more, 0.70 D or more, about 0.60 D or more, about 0.50 D or more, about 0.40 D or more, about 0.30 D or more, about 0.25 D or more or about 0.20 D or more. In other embodiments, the power profile or curvature of the central optical zone, nasal optical zone and the temporal optical zone of the ophthalmic lens may be selected such that the magnitude of asymmetry between the nasal optical zone and the central and/or temporal optical zone is in the range of 0.75 D to 0.50 D, 0.50 D to 0.25 D or 0.25 D to 0.10 D.

The refractive power profile of the optical zone or curvature or both determine the focal length. The options of having either a substantially constant power profile in an optical zone or a variable power profile across the optical zone also applies to the lens structures shown in FIGS. 7-10.

Figure 8:
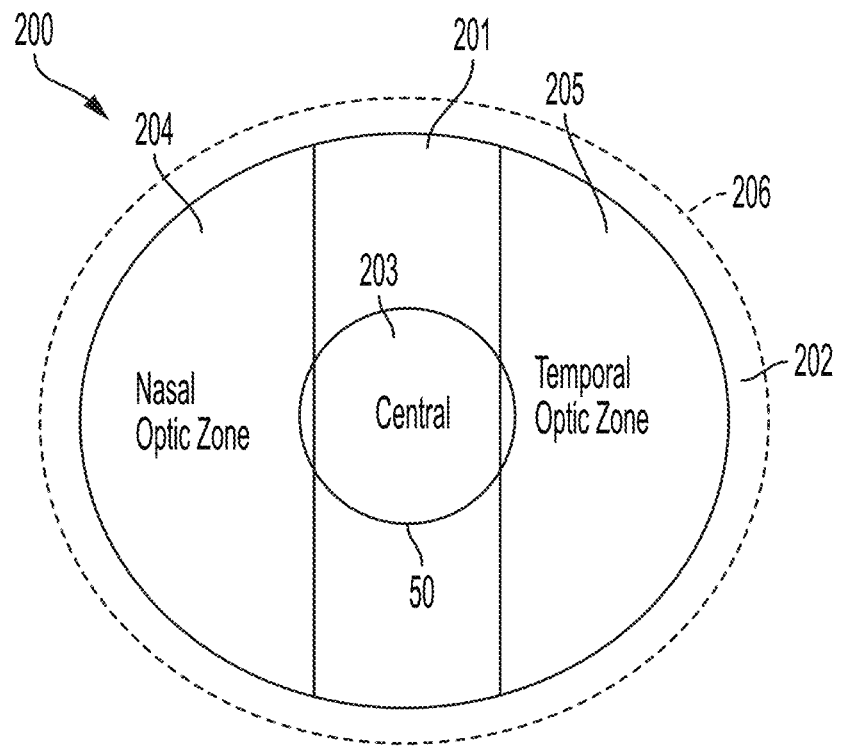
FIG. 8 illustrates another example of a contact lens with asymmetric profiles in accordance with some embodiments described herein.

In the example shown in FIG. 8, the lens 200 has a central optical zone 203 extending along the vertical meridian of the lens 200. The central optical zone 203 has a constant power from the center to the periphery of the optic zone in both directions. The width of the meridian is in the range from about 0.5 mm to about 3 mms (e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm) (e.g., about 0.5-1 mm, 0.75-1.25 mm, 1-1.5 mm, 1.25-1.75 mm, 1.5-2 mm, 1.75-2.25 mm, 2-2.5 mm, 2.25-2.75 mm, or 2.5-3 mm). The power profile of the lens 200 varies between the nasal optic zone 204 and temporal optic zone 205 on either side of the central zone 203 and selected to maintain an existing asymmetry or adjust the asymmetry to a desired level to control the progression of myopia as described for the example shown in FIG. 8.

Figure 9:
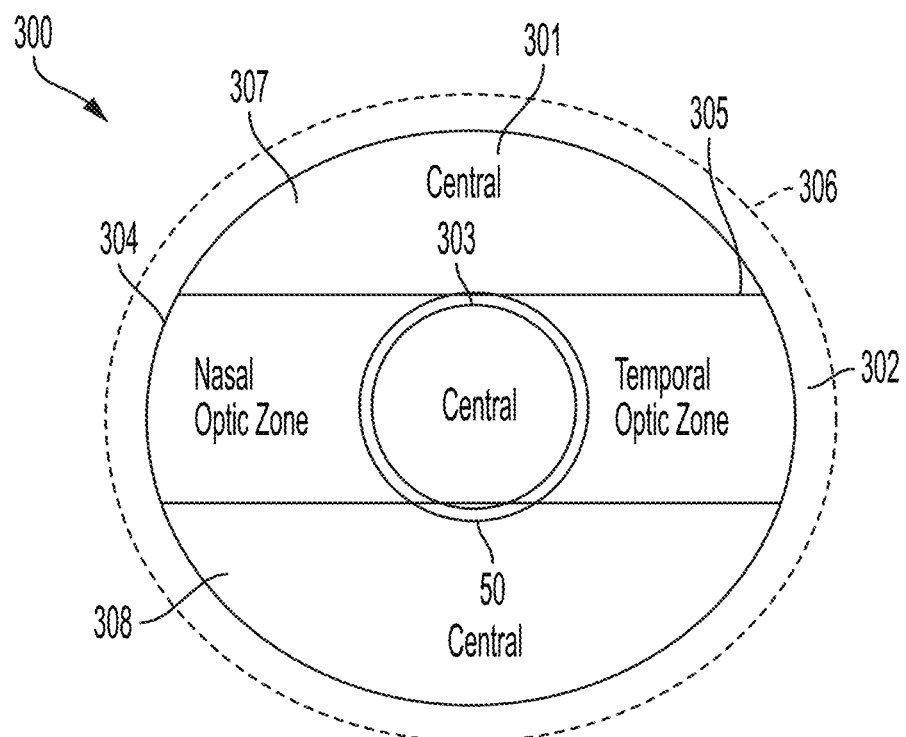
FIG. 9 illustrates another example of a contact lens with asymmetric profiles in accordance with some embodiments described herein.

In the example shown in FIG. 9, the lens 300 has a central optical zone 303 between approximately 0.5 mm to 3 mm (e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm) (e.g., about 0.5-1 mm, 0.75-1.25 mm, 1-1.5 mm, 1.25-1.75 mm, 1.5-2 mm, 1.75-2.25 mm, 2-2.5 mm, 2.25-2.75 mm, or 2.5-3 mm) in diameter with a refractive power selected to correct for the central refractive error of the eye. In the horizontal meridian, the power profile of the lens 300 varies between the nasal and temporal optic zones 304, 305 on either side of the central optic zone 303, as described for the example shown in FIG. 8. The nasal and temporal optic zones 304, 305 have a height of approximately 0.5 mm to 3 mm (e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm) (e.g., about 0.5-1 mm, 0.75-1.25 mm, 1-1.5 mm, 1.25-1.75 mm, 1.5-2 mm, 1.75-2.25 mm, 2-2.5 mm, 2.25-2.75 mm, or 2.5-3 mm), which may be selected to match the diameter of the central optic zone 303, although in other embodiments the height of these zones may be more or less than the diameter of the central optic zone 303. The nasal and temporal optic zones 304, 305 both extend from the central optic zone 303 to the edge of the optic zone 301 of the lens 300. The central optic zone 303 is extended into the regions 307, 308 outside of the peripheral optic zone. In other words, in this example, in the optic zone 301, the lens 300 has a power selected to correct for the central refractive error of the eye in all regions outside of the nasal and temporal optic zones 304, 305.

Figure 10:
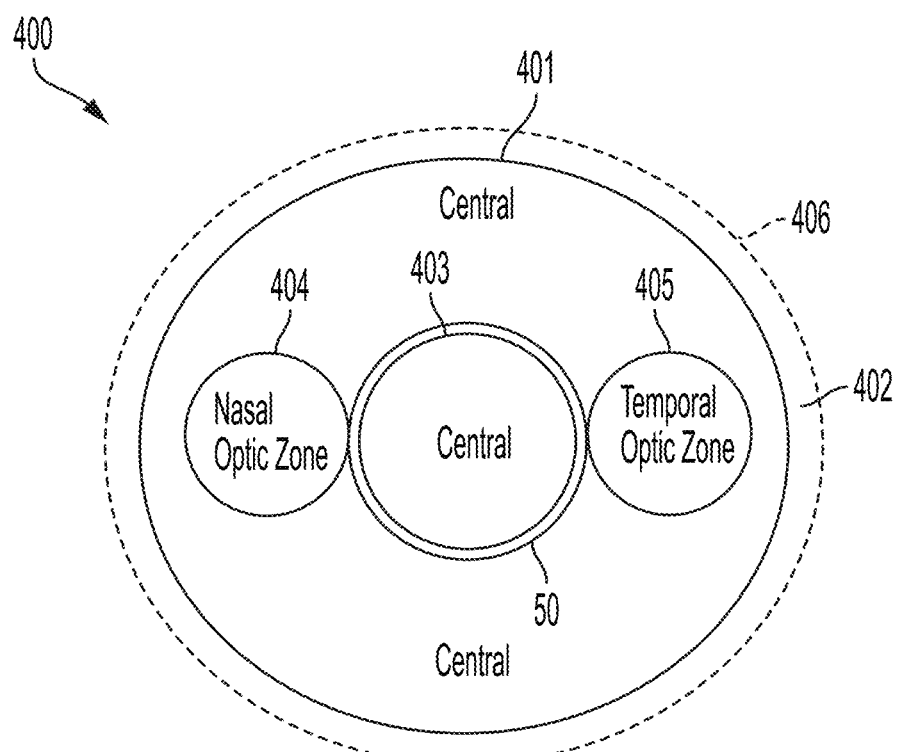
FIG. 10 illustrates another example of a contact lens with asymmetric profiles in accordance with some embodiments described herein.

In the example shown in FIG. 10, the lens 400 has a central optic zone 403 between approximately 0.5 to 3 mm (e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm) (e.g., about 0.5-1 mm, 0.75-1.25 mm, 1-1.5 mm, 1.25-1.75 mm, 1.5-2 mm, 1.75-2.25 mm, 2-2.5 mm, 2.25-2.75 mm, or 2.5-3 mm) in diameter that corrects for the central refractive error. In the horizontal meridian, the power profile of the lens varies between the nasal and temporal optic zones 404, 405 on either side of the central optic zone 403. The nasal temporal zone 404 and temporal optic zone 405 correct for the defocus measured in the temporal and nasal quadrants of the peripheral retina respectively, as described above with reference to the example shown in FIG. 8. Both the nasal and temporal optic zones 404, 405 have an oblong shape of width of about 3.0 mm to 5.0 mm (e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm) (e.g., about 0.5-1 mm, 0.75-1.25 mm, 1-1.5 mm, 1.25-1.75 mm, 1.5-2 mm, 1.75-2.25 mm, 2-2.5 mm, 2.25-2.75 mm, or 2.5-3 mm). These zones need not be oblong and could be other shapes, like circular or substantially rectilinear. The remainder of the lens carries the same power profile as the central optic zone.

For each of the examples shown in FIGS. 7-10, there may be a transition zone connecting the central optical zone (and any other region with the same power profile as the central optical zone) to the peripheral optical zones (consisting of the nasal and temporal optical zones). The transition zone is at the boundary of the central and nasal or temporal optical zones and can vary in width from about 0.25 mm to about 1.0 mm. The transition zone bridges the difference in power profile and in some embodiments is shaped to provide a smooth curve transition between the zones. In other embodiments, there may be a point on the lens where the central optical zone finishes and the peripheral optical zone commences.

As will be appreciated from the description herein, including but not limited to the examples shown in FIGS. 7-10, the shape and layout of the optical zones in a contact lens may be varied substantially, creating a large range of different embodiments. By way of example, the central optical zone 103, 203, 303, 403 may be configured to maintain an asymmetry of the retina about a vertical meridian of the retina through the fovea.

The lens power profile may not consider the refractive error state of the eye in the vertical direction, as differences along vertical meridians are not considered as important. However, in other embodiments, the refractive error state of the eye in the vertical direction may also be corrected, in the same way as described herein for the horizontal direction. In other words, the relative curvature of field naturally occurring in the eye in the vertical direction may also be measured and the lens may include upper and lower optic zones to control the curvature of field for the lower and upper portions of the peripheral retina respectively. Where there is asymmetry in the vertical direction, this may be accounted for in the same manner as asymmetry in the horizontal direction. Where both the horizontal and vertical directions are controlled, the peripheral image may be controlled in all quadrants of the eye.

The examples shown in FIGS. 7-10 show a central optic zone 103, 203, 303, 403. In the examples, a central optic zone of diameter or width of about 0.5 to 3.0 mm (e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm) (e.g., about 0.5-1 mm, 0.75-1.25 mm, 1-1.5 mm, 1.25-1.75 mm, 1.5-2 mm, 1.75-2.25 mm, 2-2.5 mm, 2.25-2.75 mm, or 2.5-3 mm) is provided. The size of the central optic zone may be selected regarding to the pupil diameter of the recipient of the lens or having regard to the average pupil diameter of a population sample most representative of the recipient or a sample representing the general population. Generally, a larger central optic zone allows for clearer vision, particularly if the central optic zone has a constant or substantially constant power profile across the area of the pupil. However, a lens with a smaller central optic zone may be required for some recipients where control of peripheral defocus close to the fovea is needed. Some sacrifice of on axis image quality may then result.

Also, the central optic zone 103, 203, 303, 403 may have a power profile selected to correct on-axis vision, with a substantially uniform power across its diameter in all or substantially all directions. Having a central optic zone may be advantageous in reducing or minimizing defocus of the image received by the fovea. In some embodiments, the power profile of the central optic zone may be allowed to vary to some extent. For example, the lens may be designed to have a power profile that progressively changes from the center point of the lens out to the nasal and temporal optic zones. The power at the center point of the lens may be selected to correct on-axis vision, or selected to provide substantially clear vision on axis.

Figure 11:
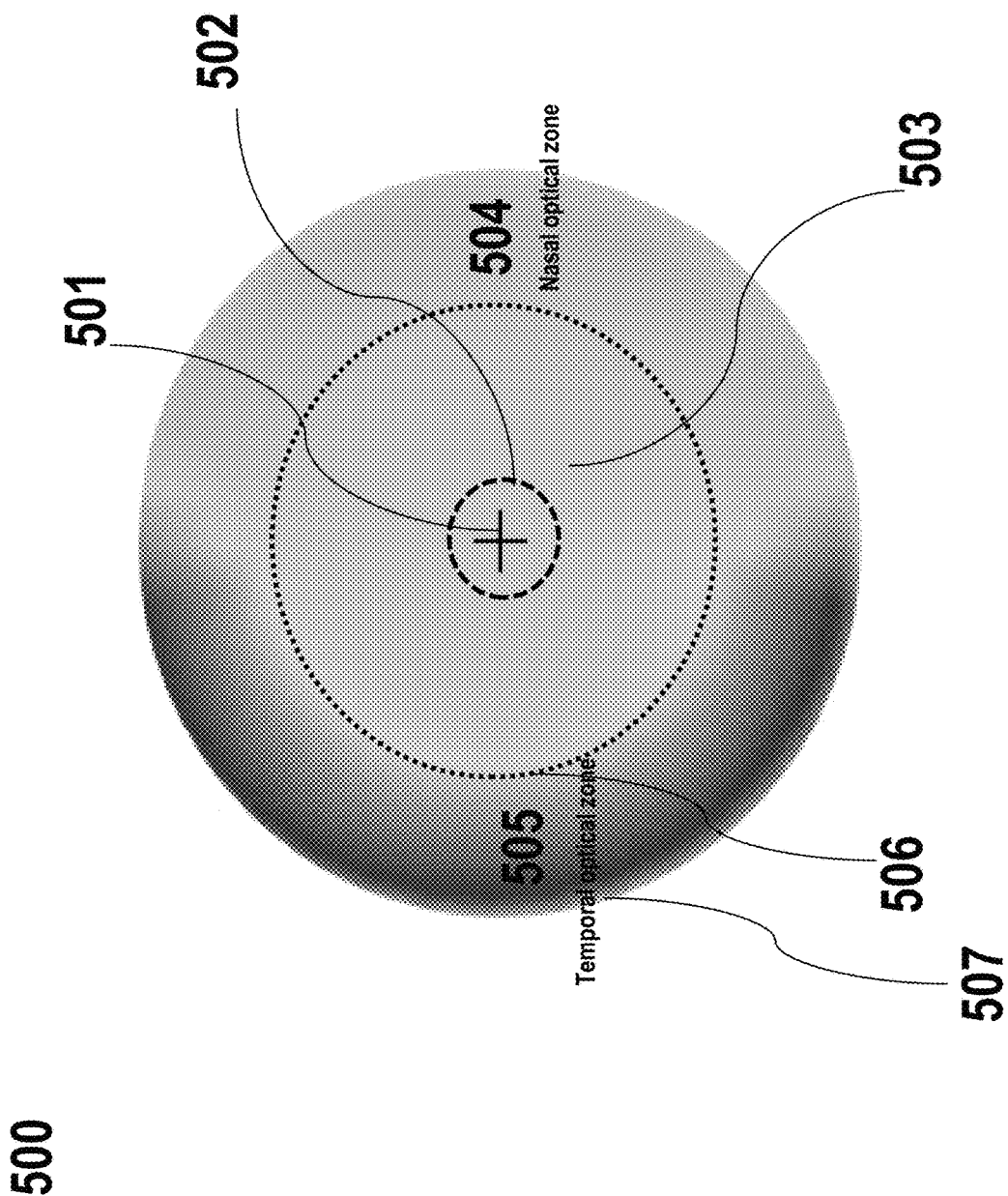
FIG. 11 illustrates an example of a spectacle lens with asymmetric profiles in accordance with some embodiments described herein.

The contact lenses shown in FIGS. 7-10 may be silicone hydrogel lenses, rigid lenses, scleral lenses or hybrid lenses. Similar lens designs may be made for spectacle lenses and corneal implants. For both these types of lenses the carrier portion is not required. A suitable structure for spectacle lenses may be like that shown in FIG. 8, except with a central optic zone of a width of about 8 to 20 mm (e.g., 8, 8, 10, 11, 12, 13, 14, 15, 16, 17, 18, 19, or 20 mm). Some embodiments of spectacle lens may have a large transition zone between the central optic zone and the peripheral optic zone, so as to avoid visible lines on the lenses and to reduce interference with the clarity of vision of the wearer when their eyes are not directed straight ahead. For example, FIG. 11 illustrates an example of a spectacle lens 500 with an asymmetric profile in accordance with some embodiments described herein. The spectacle lens blank has an optical center 501 and is 60 mm in diameter. The central optical zone 503 is 20 mm in diameter and is designed to clear vision at all or substantially all distances (assuming that the eye can accommodate to provide in focus near vision) a right eye fitted with the spectacle. In certain embodiments, the central optical zone may be oval, elliptical, cylindrical or asymmetrical in shape. Also, the central optic zone 503 may have a power profile selected to correct on-axis vision, with a substantially uniform power across its diameter in all or substantially all directions. In some embodiments, the power profile of the central optic zone may be allowed to vary to some extent. For example, the lens may be designed to have a power profile that progressively changes from the center point of the lens out to the nasal and temporal optic zones. The peripheral optical portion of the spectacle lens may be divided into two zones: nasal optical zone 504 and a temporal optical zone 505. The power profile of the lens varies between the nasal optical zone 504 and temporal optic zone 505 on either side of the central optic zone. In some embodiments, the optical center of the lens may be fitted to the center of the pupil 502 but may be fitted to vary and can be fitted in alignment with for example, the lower edge of the pupil. The nasal optic zone 104 is designed to address the defocus at the temporal retina and the temporal optic zone is designed to address the defocus at the nasal retina. The power in these zones is selected to correct for the defocus measured in the temporal and nasal quadrants of the peripheral retina respectively while maintaining or enhancing an asymmetry between the nasal retina and the temporal retina. In some embodiments, the refractive power at the central zone 503 and the nasal optical zone 504 may be substantially similar. In the temporal optical zone 505, the refractive power may be relatively more positive compared to the refractive power in the central optical zone (indicated by darker color) and increases in power from the inner edge of the temporal optical zone 506 to the outer edge of the temporal optical zone 507. In some embodiments, the relatively positive refractive power in the temporal optical zone 505 may be constant from the inner edge of the temporal optical zone 506 to the outer edge of the optical zone 506. In some embodiments, the relatively positive refractive power from the inner edge to the outer edge of the temporal optical zone may change and may be monotonic or non-monotonic. In some embodiments, the change in refractive power from the inner edge of the temporal optical zone to the outer edge of the temporal optical zone may be stepped or sinusoidal in nature. In some embodiments, the refractive power in the temporal optical zone 505 may be relatively more positive than the central optical zone 503 and/or the nasal optical zone 504 by about 2.00 D, about 1.75 D, about 1.5 D, about 1.25 D, about 1.00 D, about 0.75 D, about 0.50 D or about 0.25 D. In some embodiments, the refractive power in the temporal optical zone 505 may be relatively more positive than the central optical zone 503 and/or the nasal optical zone 504 by approximately 2.00 D to 1.50 D, 1.50 D to 1.00 D, 1.00 D to 0.50 D, 0.50 D to 0.25 D by about 2.00 D. In some embodiments, the refractive power in the temporal optical zone 505 may preferably be relatively more positive than the central optical zone 503 and/or the nasal optical zone 504 by 0.75 D to 1.00 D, 0.75 D to 1.25 D. In some embodiments, the temporal optical zone 505 may be localized to an area outside of the central optical zone and may be of any shape. In other embodiments, the temporal optical zone 505 may be arcuate and extend to the superior to the superior and inferior quadrants as illustrated in FIG. 11.

With respect to the nasal optical zone 504, in this particular example, the power is constant across the nasal optical zone. In some embodiments, the power may vary across the nasal optical zone 504. In certain embodiments, the nasal optical zone 504 may be localized to an area outside of the central optical zone and may be of any shape. In some embodiments, the nasal optical zone 504 may be arcuate and extend to the superior to the superior and inferior quadrants as illustrated in FIG. 11.

Figure 12:
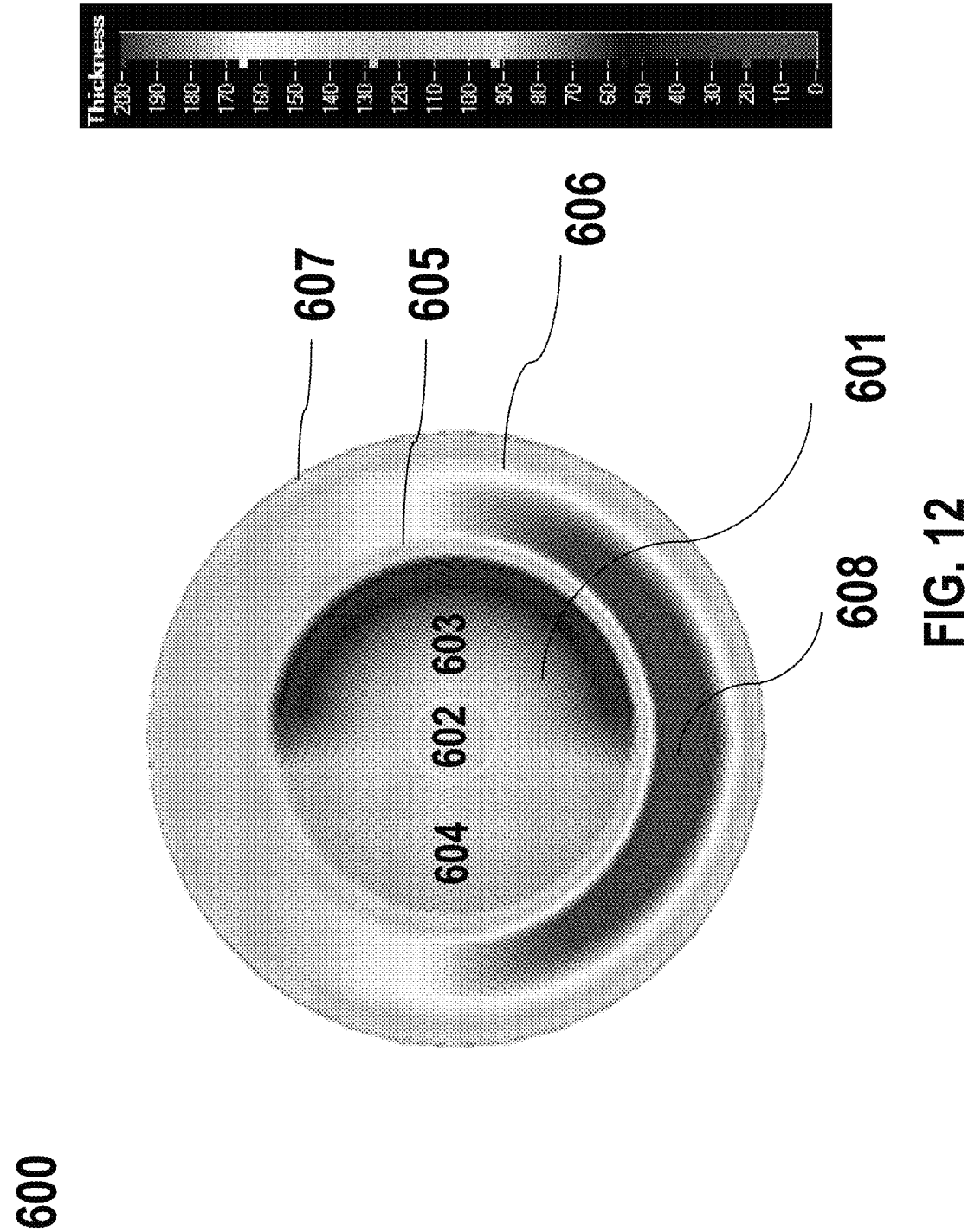
FIG. 12 illustrates another example of a contact lens with asymmetric power profile in accordance with some embodiments described herein.

FIG. 12 is an example of an embodiment of a contact lens with an asymmetric profile to enhance the asymmetry from the nasal to the temporal retina in some eyes or to create asymmetry in other eyes in accordance with the teachings described herein. The contact lens 600 is for a left eye, has a total diameter of 14.0 mm, an optical zone 601, a peripheral carrier portion 606 and a lens edge 607. The central optical zone 601 is 8 mms in diameter and is connected with the peripheral carrier 606 with a transition zone 605. The optical zone has a central zone 602 that corrects for the distance refractive error and has a temporal optical zone 603 with a different focal length to the focal length of central zone 602. The nasal optical zone 604 has the same focal length as the central optical zone 602. In the temporal optical zone 603, the focal length gradually becomes shorter from center to periphery (indicated by darker areas) or the refractive power becomes relatively more positive from the center to the periphery towards the carrier portion. The peripheral carrier portion 606 is 3 mms to either side of the optic zone. The peripheral carrier portion incorporates a prism ballast 608 inferiorly. The thickness of the prism ballast 608 in the peripheral carrier is variable and is designed to orient the lens on the eye and provide stability.

Corneal implants may be shaped to create a corneal surface profile that results in the refractive characteristics described. An orthokeratology lens may similarly reshape the cornea to achieve the relative curvature of field required for the peripheral retina. A retinal implant or a scleral implant may create a retinal profile that results with the image formation at the nasal retina having more myopic defocus relative to the image formation at the central retina and/or temporal retina.

In some embodiments, a collection of lenses or a lens series may be provided from which a selection is made for individual recipients. For example, for each power in the central optic zone, there may be a selection of asymmetric peripheral optic zones. In some embodiments, the ophthalmic lens series may comprise first and second ophthalmic lenses. The first ophthalmic lenses may comprise a central optical zone with a first focal length configured to correct the refractive error of the eye at distance and/or provide clear vision for distance viewing, a temporal optical zone with a second focal length different to the first focal length and a nasal optical zone with a third focal length different to the first focal length wherein there is no difference between the second focal length and the third focal length. The second ophthalmic lens may comprise a central optical zone with a first focal length configured to correct the refractive error of the eye at distance and/or provide clear vision for distance viewing, a temporal optical zone with a second focal length different to the first focal length and a nasal optical zone with a third focal length different to the first focal length wherein there is a difference between the second focal length and the first and/or third focal length so as to induce asymmetry. Depending on the magnitude of asymmetry a particular patient has, a first or second ophthalmic lens may be selected to reduce the risk of progression of myopia of an eye.

The selection may be made with reference to a population norm and the deviation for the population. Where there a significant variations in classes of recipients, different population norms may be constructed for each class. The number of selections for each power in the central optical zone may vary.

Figure 13:
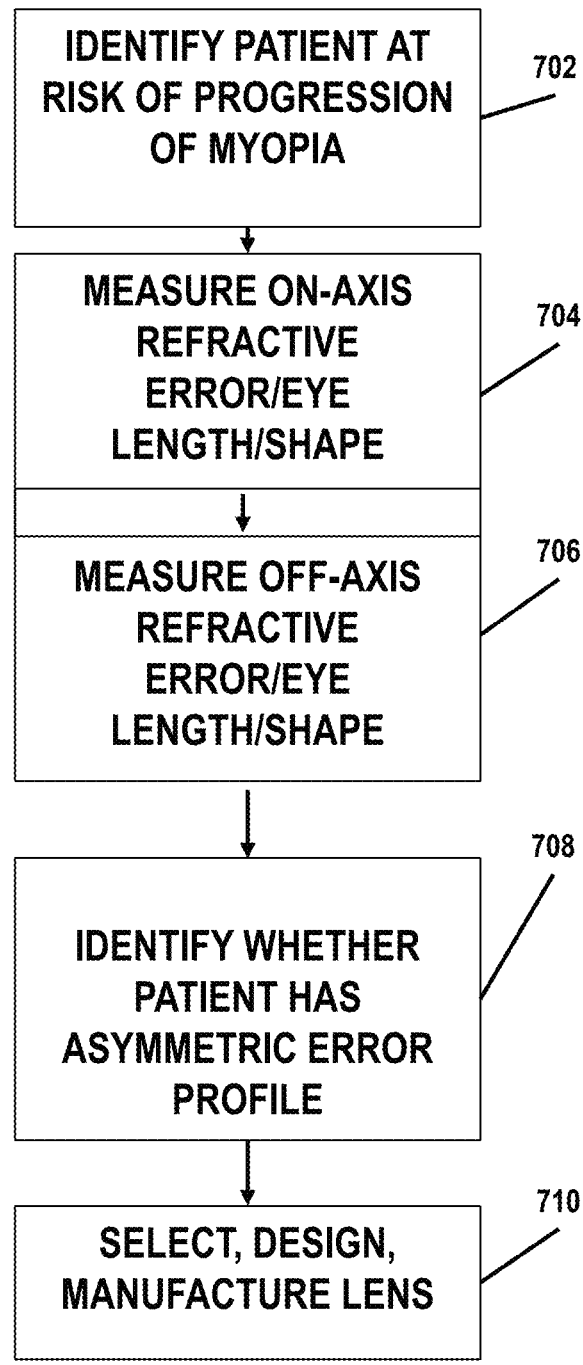
FIG. 13 is a flow chart of a method for controlling the progression of myopia in accordance with some embodiments described herein.

FIG. 13 is a flow chart of a method for controlling the progression of myopia in accordance with some embodiments described herein. In step 702 a patient is identified with refractive error. This identification step may be achieved by an examination of the history of on-axis refractive error of a patient, for example over the past 6 months or 1 to 3 years, or longer. Alternatively, the identification step 702 may be replaced with identification of a patient that has refractive error without reference to any history of error or its progression.

In step 704 the on-axis refractive error is measured. This measurement is used to identify the required correction on-axis. For example, the patient may be measured as having refractive error of −3 D, in which case the central optic zone of the lens, for example the central optic zone 103, 203, 303, 403 shown in FIGS. 7-10 may be selected to have a power to correct this error.

In step 706 the off-axis refractive error is measured. Measurements are taken for off-axis field angles nasally and temporally (e.g., at 20, 30 and/or 40 degrees). As previously described, variation in field of curvature for vertical angles may be ignored, but may be measured and included in the lens design if required. Step 706 may comprise taking a measurement at a single angle in the nasal and temporal directions, for example at 20 or 30 degrees relative to the on-axis direction. In some embodiments, the desired angle may be 20 degrees. Alternatively, step 706 may comprise taking measurements at more than one angle in the nasal and temporal directions. For example two measurements may be taken at 15 and 30 degrees, three measurements taken at 15, 30 and 35 degrees or six measurements taken at 5, 10, 15, 20, 25 and 30 degrees. The angle need not be a multiple of five, these angles being described for illustrative purposes only. More than one measurement may be taken at a single angle and these may be combined, for example through averaging or otherwise or may be subject to evaluation, for example with reference to the position of the eye when the measurement was taken, with the measurement expected to be the most accurate selected.

Depending on the instrument used, step 706 may include separate steps for measuring the refractive characteristics of an eye at each required angle relative to the optical axis of the eye. For example, this may be required if the patient has to be physically moved or asked to move their line of sight, or if the instrument needs to be physically moved relative to the patient's eye to obtain the measurements.

In step 708, an identification of whether the patient has an asymmetric error profile is made. In particular, a determination of whether the nasal retina has more error than the temporal retina is made.

In step 710 the measurements are compared to available lenses with differing power across the horizontal meridian for the best match, or a new lens design is formed for manufacture with the required power profile for the eye. As discussed above, the power profile may correct for the on-axis refractive error measured in step 704 in the central optic zone and have a power selected with regard to the refractive characteristics of the eye in the nasal and temporal peripheral regions such that the amount of correction maintains an existing asymmetry or adjust the asymmetry to a desired level to control the progression of myopia.

For example, the power profile may be selected to place the image of peripherally viewed objects as close as possible to the retina while maintaining the asymmetry of the patient's eye.

Alternatively, the power profile may be selected to place the image of peripherally viewed objects at another position relative to the retina where that is viewed as potentially providing benefit.

Example 1

To assess the effects of peripheral refractive error asymmetry over time on myopia progression, the eyes of more than 500 children with myopia were studied. The purpose of the study was to assess changes in the nasal to temporal asymmetry in the peripheral refraction profiles of individuals, at 20 and 30 degrees visual fields, over time and as a function of myopic progression.

In the study, unaided peripheral refraction data using eye mapper equipment (i.e., the BHVI Eyemapper) were assessed at the 1 month, 12 month and 24 month time points. Data was available for 533 children (at 1 month) aged between 7 and 13 years. At 12 months and 24 months, data was available for 308 and 154 children, respectively. The relative peripheral refraction from 20 degrees nasal to 20 degrees temporal was used to determine the slope (D/degree). Curvature of each eye (30 degrees nasal to temporal) was determined using a second order coefficient of a quadratic fit (i.e. deviation from a flat line). Annual progression data was used to group eyes into 3 groups (<=0.25 D [low], 0.26 D to 0.74 D [medium], >=0.75 D [high]). Slope and curvature coefficients were compared between progression groups and between three time points using linear mixed models to account for repeated effects with posthoc p value corrections.

The data demonstrated that, on average, there was more asymmetry in the peripheral refraction profiles of children with lower rates of future myopia progression ($p<0.001$, slope of low progressors=−0.013 D, medium progressors=−0.01 D, high progressors=−0.001 D). The magnitude of asymmetry did not change between visit ($p>0.05$). Over time, the curvature increased significantly in the medium and high progressing children ($p<0.05$) but the magnitude of asymmetry remained the same.

While the magnitude of relative peripheral hyperopia (i.e., curvature) was increasing with increasing myopia, the magnitude of asymmetry did not change over time. Moreover, higher levels of asymmetry were associated with lower levels of myopia progression.

These results suggest that asymmetry in the peripheral refraction profile may play a role in myopia progression.

Example Set A

A1. A lens for a myopic eye, the lens comprising: a horizontal axis that includes a center point of the lens and extends across the lens from the most nasal side of the lens to the most temporal side of the lens when the lens is in an as worn position, a central optic zone with a first power profile for providing images to be received by the retina on the fovea of the eye, the central optic zone comprising the center point of the lens, a temporal optic zone with a second power profile, different than the first power profile, for providing images to be received anterior to or on the peripheral retina on a nasal side of the eye, the temporal optic zone located on a temporal side of the lens and comprising a region along the horizontal axis, and a nasal optic zone with a third power profile, different from the first power profile, for providing images to be received anterior to or on the peripheral retina on a temporal side of the eye, the nasal optic zone located on a nasal side of the lens and comprising a region along the horizontal axis, wherein the first power profile is selected to provide clear or acceptable vision and the second and third power profiles are selected such that the second power profile is relatively more positive than the first and third power profile so as to affect the progression of myopia by inducing asymmetry.

A2. The lens of example A1, wherein the lens comprises an orthokeratology lens and wherein the first to third power profiles are effected as a reshaping of the cornea of the eye.

A3. The lens of examples A1 or A2, wherein the lens further comprises a lens stabilizing mechanism for orienting the lens on the eye.

A4. The lens of any of the earlier A examples, wherein the central optic zone is located between the nasal and the temporal optic zones, the central optic zone being asymmetrical about a vertical meridian through the lens, so as to extend across horizontal half meridians of the lens to different extents, wherein the vertical and horizontal meridians refer to an orientation of the lens caused by the stabilizing mechanism.

A5. The lens of any of the earlier A examples, wherein the central optic zone is not plano and includes a refractive power for correcting defocus.

A6. The lens of any of the earlier A examples, wherein the nasal optic zone has a vertical height of between 0.5 mm and 3 mm (e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm) (e.g., about 0.5-1 mm, 0.75-1.25 mm, 1-1.5 mm, 1.25-1.75 mm, 1.5-2 mm, 1.75-2.25 mm, 2-2.5 mm, 2.25-2.75 mm, or 2.5-3 mm) and the temporal optic zone has a vertical height of between 0.5 mm and 3 mm (e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm) (e.g., about 0.5-1 mm, 0.75-1.25 mm, 1-1.5 mm, 1.25-1.75 mm, 1.5-2 mm, 1.75-2.25 mm, 2-2.5 mm, 2.25-2.75 mm, or 2.5-3 mm).

A7. The lens of any of the earlier A examples, wherein the central optic zone is substantially rotationally symmetrical.

A8. The lens of any of the earlier A examples, wherein the central optic zone is elongate in a vertical direction across the lens, wherein the vertical direction is with reference to an orientation of the lens caused by the stabilizing mechanism.

A9. The lens of any of the earlier A examples, wherein the lens is a contact lens with an optic zone and a carrier and wherein the central optic zone extends in the vertical direction across substantially the entire optic zone.

Example Set B

B1. A lens for affecting a progression of myopia in an eye, the lens comprising: a central optic zone with an on-axis power to correct on-axis vision of the eye; a nasal optic zone and a temporal optic zone, wherein the nasal optic zone and the temporal optic zone have different refractive power profiles and refract light to be focused on or in front of the peripheral retina; and a lens stabilizing mechanism for orienting the lens on the eye; wherein the nasal optic zone and the temporal optic zone have a power relative to the on-axis power selected such that the nasal retina experiences relatively more myopic defocus than the temporal retina.

B2. The lens of example B1, wherein the lens comprises an orthokeratology lens and wherein the first to third power profiles are effected as a reshaping of the cornea of the eye.

B3. The lens of examples B1 or B2, wherein the lens further comprises a lens stabilizing mechanism for orienting the lens on the eye.

B4. The lens of any of the earlier B examples, wherein the central optic zone is located between the nasal and the temporal optic zones, the central optic zone being asymmetrical about a vertical meridian through the lens, so as to extend across horizontal half meridians of the lens to different extents, wherein the vertical and horizontal meridians refer to an orientation of the lens caused by the stabilizing mechanism.

B5. The lens of any of the earlier B examples, wherein the central optic zone is not plano and includes a refractive power for correcting defocus.

B6. The lens of any of the earlier B examples, wherein the nasal optic zone has a vertical height of between 0.5 mm and 3 mm (e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm) (e.g., about 0.5-1 mm, 0.75-1.25 mm, 1-1.5 mm, 1.25-1.75 mm, 1.5-2 mm, 1.75-2.25 mm, 2-2.5 mm, 2.25-2.75 mm, or 2.5-3 mm) and the temporal optic zone has a vertical height of between 0.5 mm and 3 mm (e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm) (e.g., about 0.5-1 mm, 0.75-1.25 mm, 1-1.5 mm, 1.25-1.75 mm, 1.5-2 mm, 1.75-2.25 mm, 2-2.5 mm, 2.25-2.75 mm, or 2.5-3 mm).

B7. The lens of any of the earlier B examples, wherein the central optic zone is substantially rotationally symmetrical.

B8. The lens of any of the earlier B examples, wherein the central optic zone is elongate in a vertical direction across the lens, wherein the vertical direction is with reference to an orientation of the lens caused by the stabilizing mechanism.

B9. The lens of any of the earlier B examples, wherein the lens is a contact lens with an optic zone and a carrier and wherein the central optic zone extends in the vertical direction across substantially the entire optic zone.

Example Set C

C1. A contact lens for affecting a progression of myopia in an eye, the contact lens comprising: a central optic zone with an on-axis power to correct on-axis vision of the eye; a nasal optic zone and a temporal optic zone, refractive power profiles and refract light to be focused in front of the peripheral retina; and a lens stabilizing mechanism for orienting the lens on the eye; wherein the nasal optic zone and the temporal optic zone have a power relative to the on-axis power selected such that the nasal retina receives relatively more positive refractive power than the temporal retina at positions equally removed from the fovea of the eye.

C2. The lens of example C1, wherein the lens comprises an orthokeratology lens and wherein the first to third power profiles are effected as a reshaping of the cornea of the eye.

C3. The lens of examples C1 or C2, wherein the lens further comprises a lens stabilizing mechanism for orienting the lens on the eye.

C4. The lens of any of the earlier C examples, wherein the central optic zone is located between the nasal and the temporal optic zones, the central optic zone being asymmetrical about a vertical meridian through the lens, so as to extend across horizontal half meridians of the lens to different extents, wherein the vertical and horizontal meridians refer to an orientation of the lens caused by the stabilizing mechanism.

C5. The lens of any of the earlier C examples, wherein the central optic zone is not plano and includes a refractive power for correcting defocus.

C6. The lens of any of the earlier C examples, wherein the nasal optic zone has a vertical height of between 0.5 mm and 3 mm (e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm) (e.g., about 0.5-1 mm, 0.75-1.25 mm, 1-1.5 mm, 1.25-1.75 mm, 1.5-2 mm, 1.75-2.25 mm, 2-2.5 mm, 2.25-2.75 mm, or 2.5-3 mm) and the temporal optic zone has a vertical height of between 0.5 mm and 3 mm (e.g., 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 mm) (e.g., about 0.5-1 mm, 0.75-1.25 mm, 1-1.5 mm, 1.25-1.75 mm, 1.5-2 mm, 1.75-2.25 mm, 2-2.5 mm, 2.25-2.75 mm, or 2.5-3 mm).

C7. The lens of any of the earlier C examples, wherein the central optic zone is substantially rotationally symmetrical.

C8. The lens of any of the earlier C examples, wherein the central optic zone is elongate in a vertical direction across the lens, wherein the vertical direction is with reference to an orientation of the lens caused by the stabilizing mechanism.

C9. The lens of any of the earlier C examples, wherein the lens is a contact lens with an optic zone and a carrier and wherein the central optic zone extends in the vertical direction across substantially the entire optic zone.

Example Set D

D1. A method of treating an eye comprising: measuring the refractive characteristics of the eye at the central and peripheral retina to obtain on-axis and off-axis measurements respectively determining from said measuring that the eye has asymmetrical off-axis refractive characteristics; and affecting the refractive properties of an ocular system comprising the eye to provide clear or acceptable vision on-axis and to control the position of the image of peripheral objects such that the resulting refractive error profile of the eye is asymmetric.

D2. The method of example D1, wherein the ocular system comprises: a lens for the eye, the lens comprising: a first zone with a first power profile selected to provide said clear or acceptable vision on-axis, a second zone with a second power profile, which controls the position of the image of peripheral objects received on the nasal side of the retina, and a third zone with a third power profile, which controls the position of the image of peripheral objects received on the temporal side of the retina, wherein at least the second and third power profiles are selected such that the nasal side of the retina experiences relatively more positive power than the temporal side of the retina at positions equally removed from the fovea of the eye.

D3. The method of example D2, wherein the lens is a lens selected from the group comprising a contact lens and a spectacle lens.

D4. The method of any of the earlier D examples, wherein the step of affecting the refractive properties of an ocular system comprising the eye comprises applying an orthokeratology lens to the eye, the orthokeratology lens providing said clear or acceptable vision on-axis and controlling the position of the image of peripheral objects by reshaping the cornea.

D5. The method of any of the earlier D examples, wherein the step of affecting the refractive properties of an ocular system comprising the eye comprises inserting a corneal implant into the eye, the corneal implant providing said clear or acceptable vision on-axis and controlling the position of the image of peripheral objects by reshaping the cornea.

Example Set E

E1. An ophthalmic system for a myopic eye, the system comprising: a central optical zone with a first focal length; a temporal optical zone with a second focal length different to the first focal length and configured to focus images at the nasal peripheral retina of the eye, and a nasal optical zone with a third focal length different from the first focal length and configured to focus images at the temporal peripheral retina of the eye, wherein the first focal length is selected to provide acceptable vision for distance and the second and third focal lengths are selected such that the second focal length is shorter than the first and third focal lengths so as to induce asymmetry.

E2. The ophthalmic system of example E1, wherein the second focal length and third focal length are substantially variable across their respective optical zones.

E3. The ophthalmic system of examples E1 or E2, wherein the ophthalmic system is a contact lens or a spectacle lens.

E4. The ophthalmic system of any of the earlier E examples, wherein the first, second and third focal lengths are determined by the lens power profile.

E5. The ophthalmic system of any of the earlier E examples, wherein the lens power profile is such that the second focal power profile is relatively more positive than the first and third surface power profiles.

E6. The ophthalmic system of any of the earlier E examples, wherein the second focal power profile is relatively more positive than the first and/or third surface power profiles by about 0.75 D.

E7. The ophthalmic system of examples E1 or E2, wherein the ophthalmic system is an orthokeratology lens or a corneal implant or refractive surgery.

E8. The ophthalmic system of any of the earlier E examples wherein the first, second and third focal lengths are determined by the effect of the ophthalmic system on the corneal curvature or corneal power or both.

E9. The ophthalmic system of any of the earlier E examples, wherein the central optical zone, temporal optical zone and the nasal optical zone are substantially unequal in surface area.

E10. The system of example E1, wherein the ophthalmic system is selected from one or more of a retinal implant, a scleral implant, a scleral buckle or a retinal prosthesis.

E11. A method for determining the progression of myopia of an eye comprising: measuring a characteristic of the eye at the fovea; measuring a characteristic of the eye at the nasal retina; measuring a characteristic of the eye at the temporal retina; and determining a magnitude of asymmetry between the characteristic of the eye at the nasal retina to the characteristic of the eye at the temporal retina and/or the fovea, wherein the magnitude of asymmetry in the ocular characteristic is used to determine the risk of progression of myopia of the eye.

E12. The method of example E11, wherein the characteristic of the eye is one or more selected from refractive error, eye length or eye shape.

E13. A method for slowing the progression of myopia of an eye comprising determining the magnitude of asymmetry of the ocular characteristic using the method recited in example E10 and affecting the ocular characteristic by providing acceptable vision on-axis and controlling the position of the ocular characteristic at the periphery of the eye such that the resulting ocular characteristic profile of the eye is asymmetric.

E14. An ophthalmic lens series for slowing progression of myopia of an eye comprising: first ophthalmic lenses; and second ophthalmic lenses; wherein, the first ophthalmic lenses comprise a central optical zone with a first focal length configured to correct the myopic error of the eye at distance and a temporal optical zone with a second focal length different to the first focal length and a nasal optical zone with a third focal length different to the first focal length, wherein there is no difference between the second focal length and the third focal length; wherein the second ophthalmic lenses comprise a central optical zone with a first focal length configured to correct the myopic error of the eye at distance and a temporal optical zone with a second focal length different to the first focal length and a nasal optical zone with a third focal length different to the first focal length, wherein there is a difference between the second focal length and the first and/or third focal length so as to induce asymmetry; and wherein a lens from the first or second ophthalmic lenses is selected based on the risk of progression of myopia of the eye.

E15. The ophthalmic lens series of example E14 comprising one or more lenses selected from a spectacle lens, contact lens, orthokeratology, corneal implants.

E16. An ophthalmic lens series for slowing progression of myopia of an eye comprising: a plurality of ophthalmic lenses; wherein the ophthalmic lenses in the series comprise a central optical zone with a first focal length configured to correct the myopic error of the eye at distance, a temporal optical zone with a second focal length different to the first focal length and a nasal optical zone with a third focal length different to the first focal length wherein the focal length between the second focal length and the first or third focal length varies resulting in asymmetry; and wherein the magnitude of asymmetry induced by the ophthalmic lenses in the series varies and an ophthalmic lens of the series is selected for the eye based on the risk of progression of myopia of the eye.

Example Set F

F1. An ophthalmic lens for a myopic eye, the lens comprising: a horizontal axis that includes a center point of the lens and extends across the lens from the most nasal side of the lens to the most temporal side of the lens when the lens is in an as worn position, a central optical zone with a first power profile for correcting the refractive error at the fovea of the eye, the central optical zone comprising the center point of the lens, a temporal optical zone with a second power profile, different than the first power profile, to focus images substantially close to or on the nasal peripheral retina, the temporal optical zone located temporally when in a worn position and comprising a region along the horizontal axis, and a nasal optical zone with a third power profile, different from the first power profile, to focus images substantially close to or on the temporal peripheral retina, the nasal optical zone located nasally when in a worn position and comprising a region along the horizontal axis, wherein the second and third power profiles are selected such that the second power profile is relatively more positive than the first and third power profile so as to induce asymmetry.

F2. The lens of example F1, wherein the ophthalmic lens is a spectacle lens.

F3. The lens of example F1, wherein the ophthalmic lens comprises an orthokeratology lens and wherein the first to third power profiles are effected as a reshaping of the cornea of the eye.

F4. The lens of example F1, wherein the ophthalmic lens is a contact lens and further comprises a lens stabilizing mechanism for orienting the lens on the eye.

F5. An ophthalmic lens for affecting a progression of myopia in an eye, the lens comprising: a central optical zone with an on-axis power to correct on-axis vision of the eye; a nasal optical zone and a temporal optical zone, wherein the nasal optical zone and the temporal optical zone have different refractive power profiles and refract light to be focused on or in front of the peripheral retina; and wherein the nasal optic zone and the temporal optic zone have a power relative to the on-axis power selected such that the nasal retina experiences relatively more myopic defocus than the temporal retina.

F6. The lens of example F5, wherein the lens is one of a contact lens or a spectacle lens.

F7. A contact lens for affecting a progression of myopia in an eye, the contact lens comprising: a central optical zone with an on-axis power to correct on-axis refractive error of the eye; a nasal optical zone and a temporal optical zone, refractive power profiles and refract light to be focused in front of the peripheral retina; and a lens stabilizing mechanism for orienting the lens on the eye; wherein the nasal optical zone and the temporal optical zone have a power relative to the on-axis power selected such that the nasal retina receives relatively more positive refractive power than the temporal retina at positions equally removed from the fovea of the eye.

F8. The lens of any of the earlier F example, wherein the central optic zone is located between the nasal and the temporal optic zones, the central optic zone being asymmetrical about a vertical meridian through the lens, so as to extend across horizontal half meridians of the lens to different extents, wherein the vertical and horizontal meridians refer to an orientation of the lens caused by the stabilizing mechanism.

F9. The lens of example F8, wherein the central optic zone is not plano and includes a refractive power for correcting defocus.

F10. The lens of example F5, wherein the nasal optic zone has a vertical height of between 0.5 mm and 3 mm and the temporal optic zone has a vertical height of between 0.5 mm and 3 mm.

F11. The lens of example F5, wherein the central optic zone is substantially rotationally symmetrical.

F12. The lens of example F5, wherein the central optic zone is elongate in a vertical direction across the lens, wherein the vertical direction is with reference to an orientation of the lens caused by the stabilizing mechanism.

F13. The lens of example F12, wherein the lens is a contact lens with an optic zone and a carrier and wherein the central optic zone extends in the vertical direction across substantially the entire optic zone.

F14. The lens of example F7, wherein the central optic zone is located between the nasal and the temporal optic zones, the central optic zone being asymmetrical about a vertical meridian through the lens, so as to extend across horizontal half meridians of the lens to different extents, wherein the vertical and horizontal meridians refer to an orientation of the lens caused by the stabilizing mechanism.

F15. The lens of example F14, wherein the central optic zone is not plano and includes a refractive power for correcting defocus.

F16. The lens of example F7, wherein the nasal optic zone has a vertical height of between 0.5 mm and 3 mm and temporal optic zone has a vertical height of between 0.5 mm and 3 mm.

F17. The lens of example F7, wherein the central optic zone is substantially rotationally symmetrical.

F18. The lens of example F7, wherein the central optic zone is elongate in a vertical direction across the lens, wherein the vertical direction is with reference to an orientation of the lens caused by the stabilizing mechanism.

F19. A method of treating an eye comprising: measuring the refractive characteristics of the eye at the central and peripheral retina to obtain on-axis and off-axis measurements respectively; determining from said measuring whether the eye has asymmetrical off-axis refractive characteristics; and affecting the refractive properties of an ocular system comprising the eye to provide clear or acceptable vision on-axis and to control the position of the image of peripheral objects such that the resulting refractive error profile of the eye is asymmetric.

F20. The method of example 19, wherein the ocular system comprises: A lens for the eye, the lens comprising: a first zone with a first power profile selected to provide said clear or acceptable vision on-axis, a second zone with a second power profile, which controls the position of the image of peripheral objects received on the nasal side of the retina, and a third zone with a third power profile, which controls the position of the image of peripheral objects received on the temporal side of the retina, wherein at least the second and third power profiles are selected such that the nasal side of the retina experiences relatively more positive power than the temporal side of the retina at positions equally removed from the fovea of the eye.

F21. The method of example 20, wherein the lens is a lens selected from the group comprising a contact lens and a spectacle lens.

F22. The method of example 20, wherein the step of affecting the refractive properties of an ocular system comprising the eye comprises applying an orthokeratology lens to the eye, the orthokeratology lens providing said clear or acceptable vision on-axis and controlling the position of the image of peripheral objects by reshaping the cornea.

F23. The method of example 20, wherein the step of affecting the refractive properties of an ocular system comprising the eye comprises inserting a corneal implant into the eye, the corneal implant providing said clear or acceptable vision on-axis and controlling the position of the image of peripheral objects by reshaping the cornea.

It will be understood that the embodiments disclosed and defined in this specification extends to all alternative combinations of two or more of the individual features mentioned or evident from the text or drawings. All of these different combinations constitute various alternative aspects of the present disclosure.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The invention claimed is:

1. An ophthalmic system for a myopic eye, the system comprising:
   a central optical zone with a first focal length;
   a temporal optical zone with a second focal length different to the first focal length and configured to focus images at the nasal peripheral retina of the eye, and a nasal optical zone with a third focal length different from the first focal length and configured to focus images at the temporal peripheral retina of the eye,
   wherein the first focal length is selected to provide acceptable vision for distance and the second and third focal lengths are selected such that the second focal length is shorter than the first and third focal lengths so as to induce asymmetry; and wherein the second focal power profile is relatively more positive than at least the third surface power profiles by about 0.75 D.

2. The ophthalmic system of claim 1, wherein the temporal optical zone and the nasal optical zone provide variable focal lengths across their respective optical zones and wherein the average focal length within the temporal optical zone is the second focal length and the average focal length of the nasal optical zone is the third focal length.

3. The ophthalmic system of claim 1, wherein the ophthalmic system is a contact lens or a spectacle lens.

4. The ophthalmic system of claim 3, wherein the ophthalmic system comprises a lens power profile and the first, second and third focal lengths are determined by the lens power profile.

5. The ophthalmic system of claim 1, wherein the ophthalmic system is an orthokeratology lens or a corneal implant or an eye of a patient as a result of a refractive surgery.

6. The ophthalmic system of claim 1, wherein the first, second and third focal lengths are determined by the effect of the ophthalmic system on the corneal curvature or corneal power or both.

7. The ophthalmic system of claim 1, wherein the central optical zone, temporal optical zone and the nasal optical zone are substantially unequal in surface area.

8. The ophthalmic system of claim 1, wherein the ophthalmic system is selected from one or more of a retinal implant, a scleral implant, a scleral buckle or a retinal prosthesis.

9. An ophthalmic lens for a myopic eye, the lens comprising:
a horizontal axis that includes a center point of the lens and extends across the lens from the most nasal side of the lens to the most temporal side of the lens when the lens is in an as worn position,
a central optical zone with a first power profile for correcting the refractive error at the fovea of the eye, the central optical zone comprising the center point of the lens, a temporal optical zone with a second power profile, different than the first power profile, to focus images substantially close to or on the nasal peripheral retina, the temporal optical zone located temporally when in a worn position and comprising a region along the horizontal axis, and
a nasal optical zone with a third power profile, different from the first power profile, to focus images substantially close to or on the temporal peripheral retina, the nasal optical zone located nasally when in a worn position and comprising a region along the horizontal axis,
wherein the second and third power profiles are selected such that the second power profile is relatively more positive than the first and third power profile so as to induce asymmetry; and
wherein the second focal power profile is relatively more positive than at least the third surface power profiles by about 0.75 D.

10. The lens of claim 9, wherein the ophthalmic lens is a spectacle lens.

11. The lens of claim 9, wherein the ophthalmic lens comprises an orthokeratology lens and wherein the first to third power profiles are effected as a reshaping of the cornea of the eye.

12. The lens of claim 9, wherein the ophthalmic lens is a contact lens and further comprises a lens stabilizing mechanism for orienting the lens on the eye.

13. The lens of claim 12, wherein the central optic zone is located between the nasal and the temporal optic zones, the central optic zone being asymmetrical about a vertical meridian through the lens, wherein the vertical and horizontal meridians refer to an orientation of the lens caused by the stabilizing mechanism.

14. The lens of claim 13 wherein the central optic zone is not piano and includes a refractive power for correcting defocus.

* * * * *